(12) United States Patent
Sjostrom

(10) Patent No.: US 7,485,125 B2
(45) Date of Patent: Feb. 3, 2009

(54) CUTTING INSTRUMENT

(75) Inventor: Douglas D. Sjostrom, Tewksbury, MA (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

(21) Appl. No.: 10/015,778

(22) Filed: Dec. 17, 2001

(65) Prior Publication Data

US 2003/0114875 A1 Jun. 19, 2003

(51) Int. Cl.
*A61B 17/22* (2006.01)
(52) U.S. Cl. .................................. 606/159; 604/22
(58) Field of Classification Search ................ 606/159, 606/170, 184, 185, 210, 211
See application file for complete search history.

(56) References Cited

U.S. PATENT DOCUMENTS

| | | | | |
|---|---|---|---|---|
| 1,360,016 | A | * | 11/1920 | Porter ......................... 407/54 |
| 3,082,805 | A | | 3/1963 | Royce |
| 3,614,953 | A | * | 10/1971 | Moss ......................... 606/159 |
| 3,732,858 | A | * | 5/1973 | Banko ........................ 600/566 |
| 3,906,954 | A | * | 9/1975 | Baehr et al. ................. 606/107 |
| 3,937,222 | A | * | 2/1976 | Banko ......................... 606/170 |
| 3,945,375 | A | | 3/1976 | Banko |
| 3,976,077 | A | * | 8/1976 | Kerfoot, Jr. ................. 606/107 |
| 4,167,944 | A | * | 9/1979 | Banko ......................... 606/107 |
| 4,203,444 | A | * | 5/1980 | Bonnell et al. ............... 604/22 |
| 4,493,698 | A | | 1/1985 | Wang et al. |
| 4,649,919 | A | * | 3/1987 | Thimsen et al. ............... 606/80 |
| 4,844,064 | A | * | 7/1989 | Thimsen et al. ............... 606/80 |
| 4,867,157 | A | * | 9/1989 | McGurk-Burleson et al. ......................... 606/170 |
| 5,007,917 | A | * | 4/1991 | Evans ......................... 606/170 |
| 5,116,868 | A | | 5/1992 | Chen et al. |
| 5,135,531 | A | * | 8/1992 | Shiber ........................ 606/159 |
| 5,203,653 | A | * | 4/1993 | Kudla ......................... 408/207 |
| 5,269,785 | A | | 12/1993 | Bonutti |

(Continued)

FOREIGN PATENT DOCUMENTS

EP 0 310 285 5/1989

(Continued)

OTHER PUBLICATIONS

PCT Search Report for PCT/US02/ 40294 mailing date Feb. 5, 2003, Int'l filing date Dec. 16, 2003.

(Continued)

*Primary Examiner*—Kevin T Truong
*Assistant Examiner*—Victor X Nguyen
(74) *Attorney, Agent, or Firm*—Fish & Richardson P.C.

(57) ABSTRACT

A cutting instrument includes an outer member having a cutting portion, and a helical knife coupled to the outer member for rotation relative to the outer member. At least a portion of the helical knife extends distally beyond the cutting portion. The instrument includes an inner member received within the outer member. The helical knife is at a distal end of the inner member. A method of cutting includes slicing into tissue with a helical knife to draw tissue proximally toward a cutting portion, and cutting the tissue with the cutting portion. The helical knife is provided on an inner member, and the cutting portion is provided on an outer member. Cut tissue is transported along a helical channel defined by the helical knife and aspirated through a hollow interior in the inner member.

58 Claims, 5 Drawing Sheets

U.S. PATENT DOCUMENTS

| | | | |
|---|---|---|---|
| 5,304,118 A | | 4/1994 | Trese et al. |
| 5,334,211 A | * | 8/1994 | Shiber .................... 606/159 |
| 5,383,884 A | | 1/1995 | Summers |
| 5,423,799 A | | 6/1995 | Shiu |
| 5,429,601 A | | 7/1995 | Conley et al. |
| 5,569,284 A | | 10/1996 | Young et al. |
| 5,591,187 A | | 1/1997 | Dekel |
| 5,660,186 A | * | 8/1997 | Bachir .................... 600/562 |
| 5,857,995 A | * | 1/1999 | Thomas et al. ............ 604/22 |
| 5,911,699 A | | 6/1999 | Anis et al. |
| 5,913,867 A | * | 6/1999 | Dion ...................... 606/180 |
| 6,007,513 A | | 12/1999 | Anis et al. |
| 6,053,923 A | * | 4/2000 | Veca et al. ................ 606/80 |
| 6,068,641 A | * | 5/2000 | Varsseveld ............... 606/170 |
| 6,120,147 A | | 9/2000 | Vijfvinkel et al. |
| 6,132,448 A | | 10/2000 | Perez et al. |
| 6,203,518 B1 | | 3/2001 | Anis et al. |
| 6,217,543 B1 | | 4/2001 | Anis et al. |
| 6,258,111 B1 | | 7/2001 | Ross et al. |
| 6,277,096 B1 | | 8/2001 | Cortella et al. |
| 6,443,966 B1 | * | 9/2002 | Shiu ....................... 606/159 |
| 6,482,217 B1 | * | 11/2002 | Pintor et al. ............ 606/159 |
| 6,673,023 B2 | | 1/2004 | Pflueger |
| 2002/0138021 A1 | | 9/2002 | Pflueger |
| 2002/0138091 A1 | | 9/2002 | Pflueger |

FOREIGN PATENT DOCUMENTS

| | | |
|---|---|---|
| WO | 02/076283 | 10/2002 |

OTHER PUBLICATIONS

European Patent Office, Examination Report for EPO application No. 02 797 371.8 dated May 21, 2007 (4 pages).

* cited by examiner

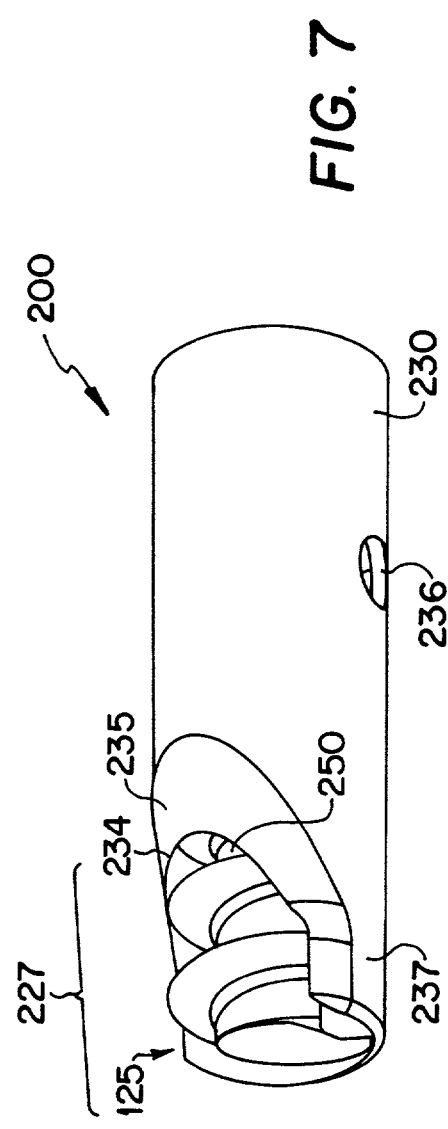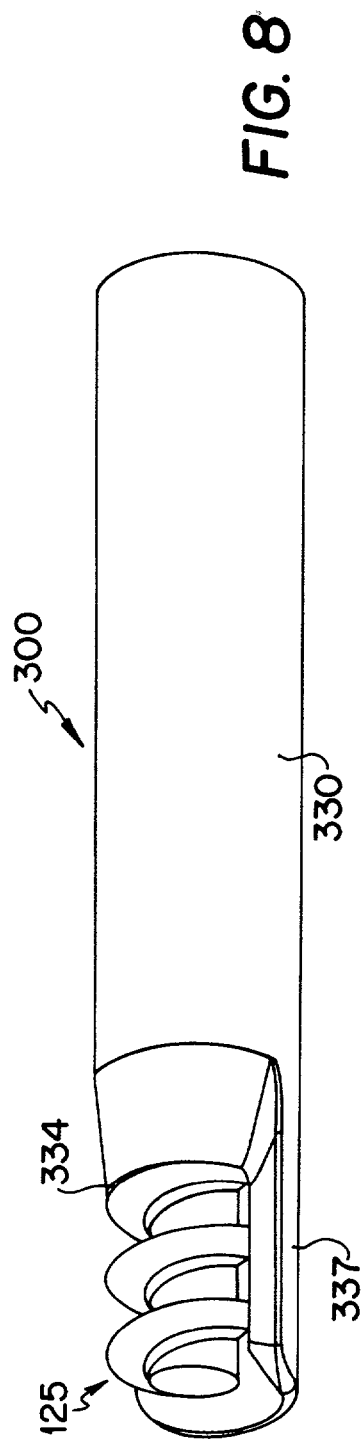

ial members is in the range of about 0.0005 to 0.002 inches.

CUTTING INSTRUMENT

TECHNICAL FIELD

This invention relates to cutting instruments, and more particularly, to a surgical cutting instrument for cutting tough fibrous tissue.

BACKGROUND

Tough fibrous tissues such as intrauterine fibroids and meniscal cartilage are difficult to resect with current arthroscopic instruments such as shaver blades. Conventional shaver blades are most effective when the tissue to be resected is soft and compliant and can be suctioned into a cutting aperture of the shaver blade. Typically, alternative resection technologies such as Laser and Radio Frequency Ablation are used to remove tougher tissues

SUMMARY

The cutting instrument of the invention divides the cutting action into two components, the first replacing aspiration to draw tissue into the blade, and the second acting to sever the tissue drawn into the blade. The first component includes slicing into the tissue with a helical knife to draw tissue against a fixed cutting edge, and the second component includes cutting the tissue into discrete pieces with the cutting edge.

According to one aspect of the invention, a cutting instrument includes an outer member having a cutting edge, and a helical knife coupled to the outer member for rotation relative to the outer member. At least a portion of the helical knife extends distally beyond the cutting edge of the outer member.

Embodiments of this aspect of the invention may include one or more of the following features.

The instrument includes an inner member received within the outer member. The helical knife is located at a distal end of the inner member. A clearance between the inner member and the outer member is in the range of about 0.0005 to 0.002 inches. The inner member defines an aspiration opening and the aspiration opening is located at a proximal end of the helical knife. The helical knife includes a helical edge and a helical channel. The helical channel has a proximal end, a distal end, and a pitch. The pitch of the helical channel increases from the distal end to the proximal end. The helical channel terminates in an aspiration opening through a wall of the inner member.

The instrument includes a hub coupling the inner member to the outer member. The outer member defines a fluid ingress opening. The fluid ingress opening is located at a distal region of the outer member.

The cutting portion is located at a distal end of the outer member and tapers to a sharp cutting edge. The cutting edge is located at a distal end of the outer member. The outer member tapers to the cutting edge. The cutting edge is a circumferential cutting edge that is, for example, circular in shape. Alternatively, the cutting edge is part-circumferential and is, for example, circular or oblong in shape. The outer member includes a shield portion extending distally from the cutting edge.

According to another aspect of the invention, a method of cutting includes slicing into tissue with a helical knife to draw tissue proximally toward a cutting portion, and cutting the tissue with the cutting portion.

Embodiments of this aspect of the invention may include one or more of the following features. The helical knife is provided on an inner member and the cutting portion is provided on an outer member. The method includes transporting cut tissue along a helical channel defined by the helical knife, and aspirating the cut tissue through a hollow interior in the inner member. Aspirating the cut tissue includes aspirating the cut tissue through an opening in a wall of the inner member. The method further includes aspirating fluid through an opening in the outer member. Conventional shaver blades rely on suction or mechanical force to introduce tissue to a blade for cutting the tissue resulting in tough tissue, such as intrauterine fibroids and meniscal cartilage, not being cut by the blade. The two component cutting action of the surgical cutting instrument of this invention overcomes this difficulty by first slicing into the tissue with a helical knife to draw the tissue against a cutting edge and then cutting the tissue into discrete pieces with the cutting edge.

The details of one or more implementations are set forth in the accompanying drawings and the description below. Other features and advantages will be apparent from the description and drawings, and from the claims.

DESCRIPTION OF DRAWINGS

FIG. 7 is a side view of the distal end of an alternative embodiment of the surgical cutting instrument.

FIG. 8 is a side view of the distal end of another alternative embodiment of the surgical cutting instrument.

Like reference symbols in the various drawings indicate like elements.

DETAILED DESCRIPTION

Figure 1:
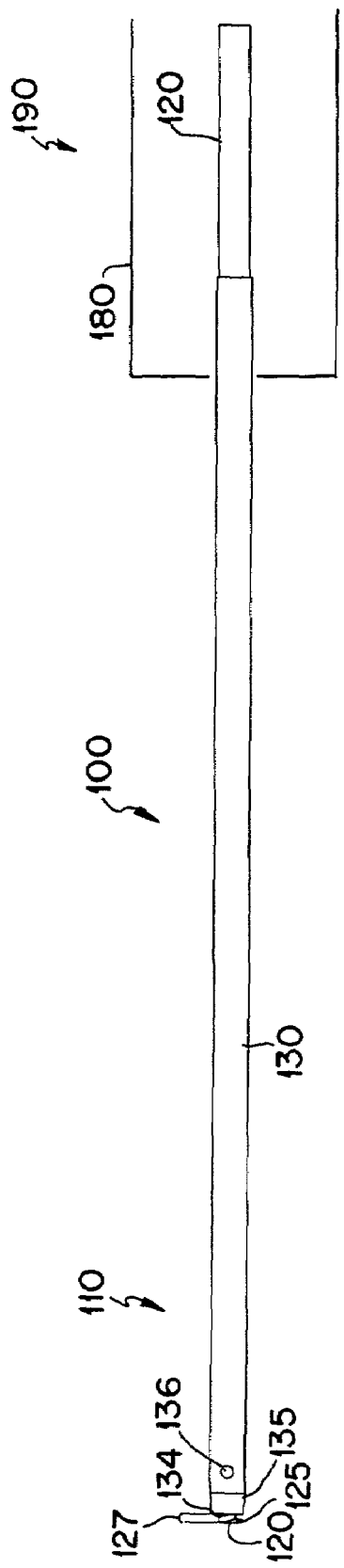
FIG. 1 is a side view of a surgical cutting instrument.

Referring to FIG. 1, a surgical cutting instrument 100 for resecting tough fibrous tissues, such as intrauterine fibroids and meniscal cartilage, includes an inner member 120 with a helical knife 125, and an outer member 130 with a cutting portion 135. Cutting portion 135 has a cutting edge 134, and a portion 127 of helical knife 125 extends distally beyond the cutting edge 134. With portion 127 of the helical knife 125 against tissue, rotation of the inner member 120 causes portion 127 of the helical knife 125 to slice into the tissue, drawing the tissue proximally along the helical knife 125 and against the cutting edge 134 of the outer member 130. Tissue is cut into discrete pieces by cutting edge 134 and the pieces are aspirated away from the surgical site through instrument 100.

The surgical cutting instrument 100 has a distal region 110 including helical knife 125 and cutting portion 135. Instrument 100 has a proximal region 190 at which the inner and outer members 120, 130 are coupled by a hub 180 (as is known for arthroscopic cutting blades having a stationary outer member and an inner member driven by a rotary driver).

The inner member 120 is received inside the outer member 130. The outer diameter of the inner member 120 and the inner diameter of the outer member 130 are close fitting. For example, the clearance between the inner and the outer members is in the range of about 0.0005-0.002 inches such that tissue drawn to the cutting portion 135 of the outer member 130 by the helical knife 125 is cut by a shearing action between the cutting portion 135 and the helical knife 125, like the cutting action of a scissors.

Figure 2:
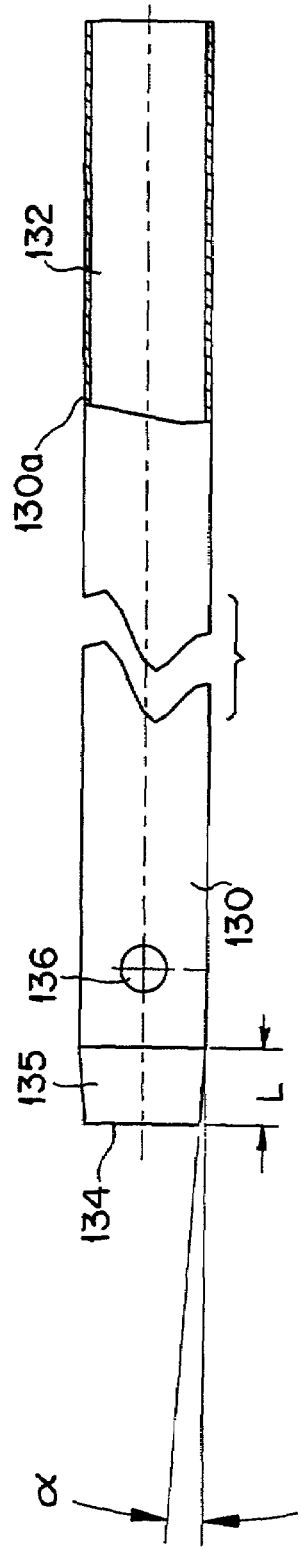
FIG. 2 is a side view in partial cross-section of the outer member of the cutting instrument of FIG. 1.

Referring to FIG. 2, the outer member 130 is tubular with a hollow interior 132. The cutting portion 135 tapers distally to the sharp, circular, circumferential cutting edge 134. The cutting portion 135 is approximately 0.10 inches in length L and tapers at an angle a of about 4°-5°. Proximate to the cutting portion 135, the outer member 130 defines an opening 136 through a wall 130a of the outer member 130. The opening 136 is an ingress for water or other fluids to enter the instrument to assist in removing cut tissue.

Figure 3:
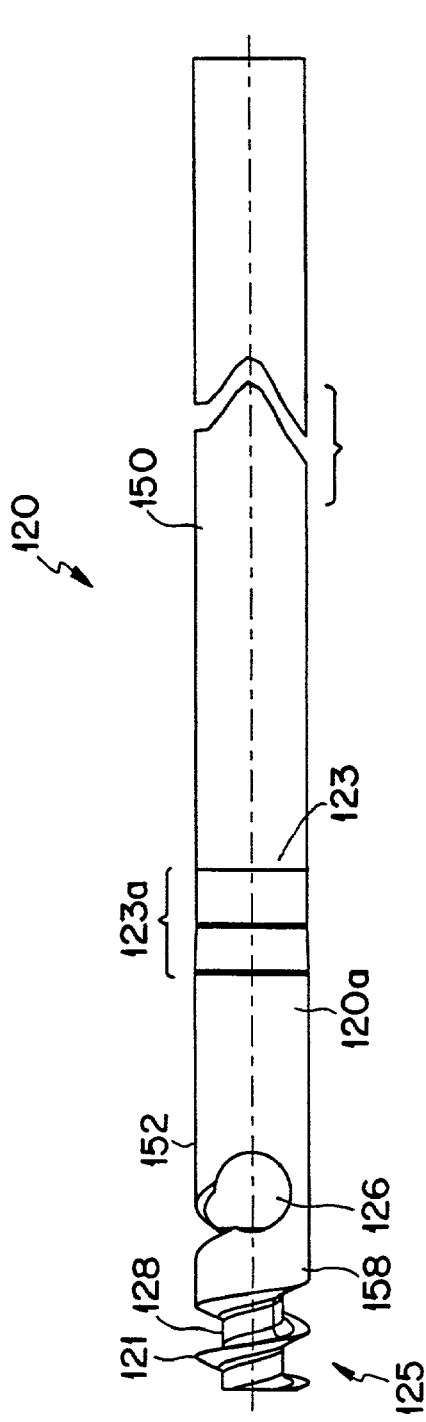
FIG. 3 is a side view in partial cross-section of the inner member and helical knife of the cutting instrument of FIG. 1.
Figure 5:
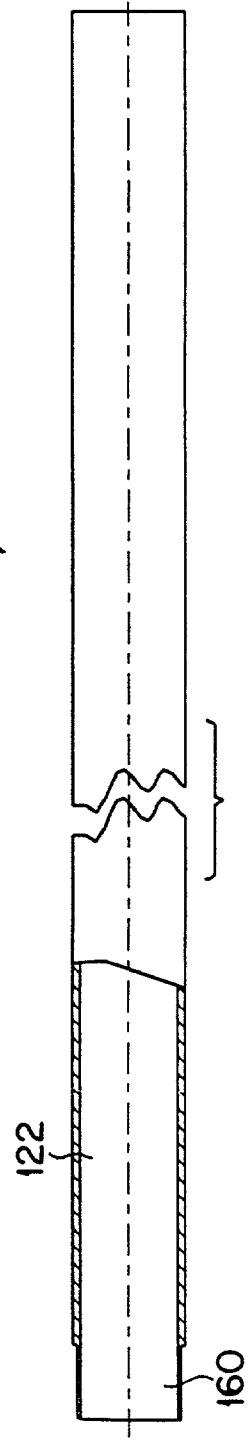
FIG. 5 is a side view of the inner member of the cutting instrument of FIG. 1.

Referring to FIGS. 3-5, the inner member 120 includes a proximal, tubular portion 150, and a distal portion 152. Proximal portion 150 defines a hollow interior 122. Distal portion 152 has a proximal section 154 defining a hollow interior 122a in fluid communication with hollow interior 122, and a solid distal section 158 defining helical knife 125. Proximal portion 150 has a distal region 160 with a decreased outer diameter, and distal portion 152 has a proximal region 162 with an increased inner diameter. To fix distal portion 152 to proximal portion 150, distal region 160 of portion 150 is received within proximal region 162 of portion 152 and the two portions are welded together in region 123a.

Figure 4A:
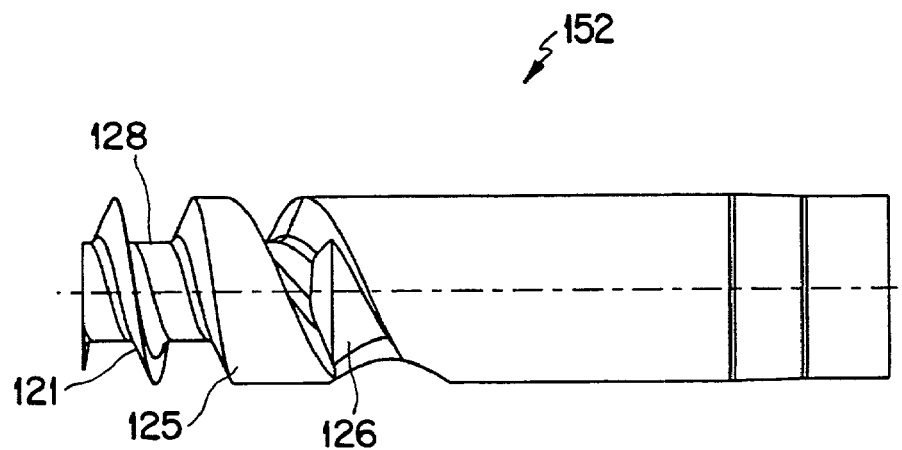
FIG. 4A is a detailed top view.
Figure 4B:
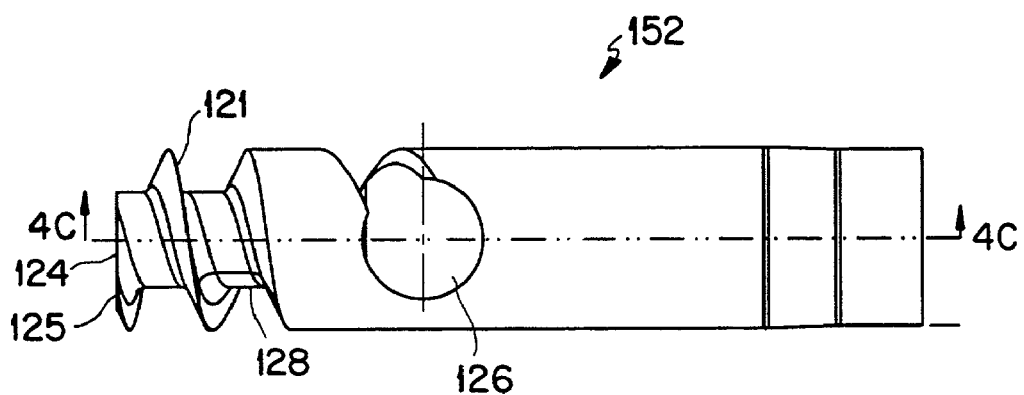
FIG. 4B is a side view.
Figure 4C:
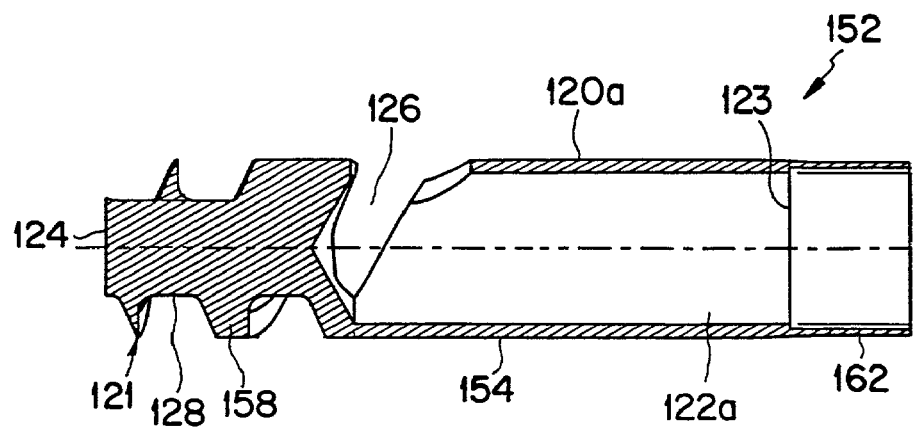
FIG. 4C is a cross-sectional view along section 4C-4C in FIG. 4B of the helical knife of the cutting instrument of FIG. 1.

Referring particularly to FIGS. 4A-4C, the helical knife 125 has a sharp-edged helix 121 and a helical channel 128. The helical channel 128 terminates proximally in an opening 126 through a wall 120a of the inner member 120. The helical knife 125 has a blunt tip 124 at its distal end. The helix 121 extends proximally from tip 124 and the pitch of the helix 121, and thus of the channel 128, increases proximally from the blunt tip 124 to the opening 126, for example, from approximately 0.065 at the blunt tip 124 of the helix 121 to 0.20 at the proximal end of the helix 121 at the opening 126. Sliced tissue is transported proximally along channel 128 to the cutting edge 134, where the tissue is cut into discrete pieces. The pieces of cut tissue are channeled through opening 126 into hollow interior 122a.

The opening 126 is an ingress for cut tissue to enter the hollow interiors 122a, 122 of the inner member 120 to be transported away. The helical portion 121 of the inner member 120 has a predetermined axial length to allow for the change in pitch to channel tissue through opening 126 without clogging opening 126. For example, the length of the helix 121 is 0.252 inches where the helical knife 125 has a length of 0.665 inches and the overall length of the inner member 120 is in the range of 6.902 to 6.932 inches.

Figure 6:
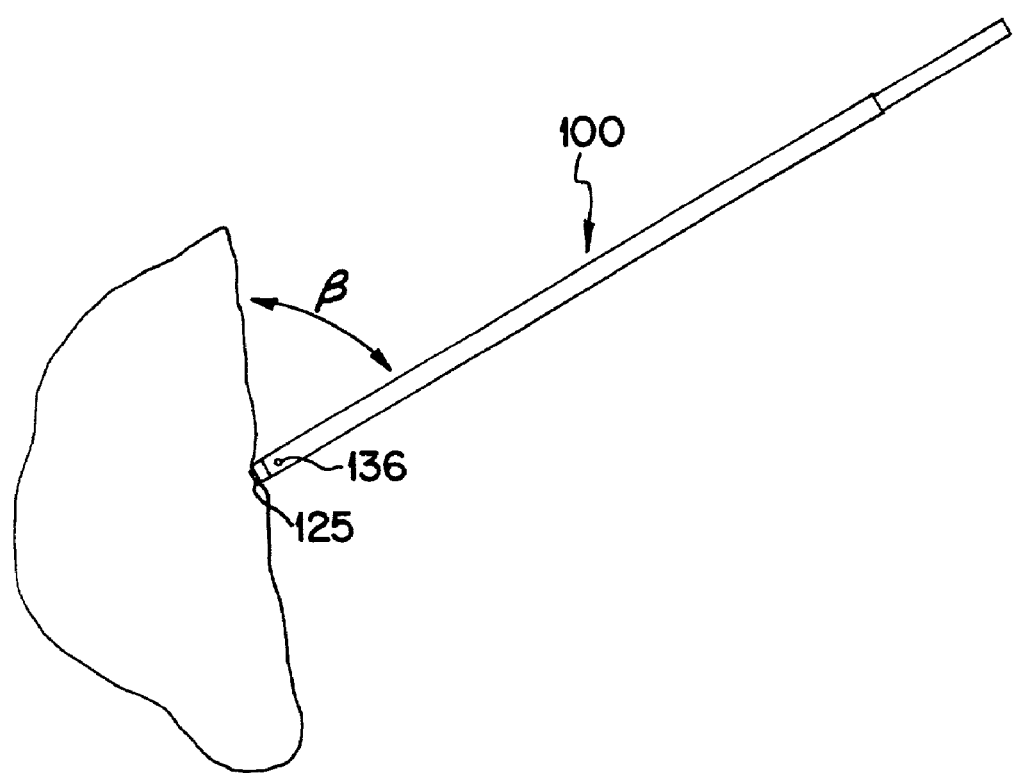
FIG. 6 illustrates use of the cutting instrument of FIG. 1.

Referring to FIG. 6, in use, an operator holds the cutting instrument 100 against the targeted tissue. The cutting instrument can be oriented with angle, β, ranging from about 15° to 345°. The helical knife 125 of the inner member 120 is rotated clockwise and helix 121 slices into the targeted tissue. The helical knife 125 channels the tissue along the helical channel 128 to the cutting portion 135 where the tissue is cut into discrete pieces against the sharpened cutting edge 134. After being cut by the cutting portion 135, the discrete pieces are drawn further along the helical channel 128 of the helical knife 125, through the opening 126 of the inner member 120 and into hollow interior 122a to be aspirated along hollow interior 122. Fluid, such as, for example, water or saline, enters through the opening 136 of the outer member 130 into the inner member 120 through the opening 126 as the discrete tissue pieces are aspirated through the inner member 120 to assist in transporting the cut tissue from the surgical site.

Other embodiments are within the scope of the following claims. For example, referring to FIG. 7, a cutting instrument 200 includes an outer member 230 with a chamfered, cutting portion 235 forming a cutting edge 234, and a shield portion 237 extending distally of cutting edge 234. Shield portion 237 extends distally beyond the distal end 124 of helical cutter 125, and circumferentially over about 180° of outer member 230 to partially cover helical knife 225, thereby protecting nearby tissue from incidental damage by the helical knife 125. Cutting edge 234 is part-circumferential, extending over about 180° of outer member 230. Rather than being perpendicular to the axis of the instrument, as in the embodiment described above, cutting edge 234 is formed at about a 45° angle to the axis of the instrument, such that cutting edge 234 has an oblong shape. Shield portion 237 and cutting edge 234 define a window 250. Helical knife 225 has a portion 227 extending distally beyond cutting edge 234 that is exposed to the tissue through window 250. As previously described, rotation of the helical knife 125 slices the helical knife 125 into targeted tissue, drawing the tissue proximally along the helical knife 125 and against the cutting portion 235 of the outer member 230 to be cut by the cutting portion 235.

Referring to FIG. 8, a surgical instrument 300 has an outer member 330 with a circular, part-circumferential cutting edge 334 formed perpendicular to the axis of the instrument, and a shield portion 337 extending distally of the cutting edge 334. Here, the shield portion 337 extends about less than 180°, for example, shield portion 337 extends about 120°, of the outer member 330 to expose more of the helical knife 125. In the embodiments of FIGS. 7 and 8, the instrument is placed tangentially against the tissue, and acts as a side cutter drawing the tissue laterally into the helical channel and axially, proximally along the helical channel to the cutting edge.

A number of implementations have been described. Nevertheless, it will be understood that various modifications may be made. For example, a third member can be disposed around the outer member to create an annulus to introduce fluid to a surgical site. Additionally, the dimensions of various parts of the cutting instrument may vary with the specific application for which the cutting instrument is used. Accordingly, other embodiments are within the scope of the following claims.

What is claimed is:

1. A cutting instrument, comprising:
an outer member having an opening at least partially bounded by a sharp cutting edge; and
a helical knife coupled to the outer member for rotation relative to the outer member, the helical knife having a flat surface at a distal end of the helical knife, the helical knife having an edge configured to slice into tough, fibrous tissue, the edge of the helical knife extending through the opening such that, during use, the edge slices into tough, fibrous tissue to draw the tough, fibrous tissue proximally along the helical knife towards the sharp cutting edge, the helical knife edge being arranged relative to the cutting edge such that the edges align in a plane substantially perpendicular to a longitudinal axis of the instrument to create a shearing action therebetween.

2. The instrument of claim 1 wherein the edge of the helical knife extends distally though the opening.

3. The instrument of claim 1 wherein the sharp cutting edge and the edge of the helical knife are configured to cut tissue therebetween by a shearing action.

4. The instrument of claim 1, further comprising:
an inner member received within the outer member, the helical knife being located at a distal portion of the inner member.

5. The instrument of claim 4 wherein the inner member defines an aspiration opening, the aspiration opening being located at a proximal portion of the helical knife.

6. The instrument of claim 5, wherein the inner member has a wall defining a hollow interior, and the aspiration opening is defined through the wall of the inner member to the hollow interior.

7. The instrument of claim 1 wherein the edge of the helical knife comprises a helical edge and the helical knife includes a helical channel.

8. The instrument of claim 7 wherein the helical channel has a proximal end, a distal end, and a pitch, the pitch of the helical channel increasing from the distal end to the proximal end.

9. The instrument of claim 7, further comprising:
an inner member received within the outer member, the helical knife being located at a distal portion of the inner member, wherein a proximal end of the helical channel terminates in an opening through a wall of the inner member.

10. The instrument of claim 1 wherein the outer member defines a fluid ingress opening through a wall of the outer member in a distal region of the outer member.

11. The instrument of claim 1 wherein the sharp cutting edge is located at a distal end of the outer member.

12. The instrument of clalm 1 wherein the outer member tapers to the sharp cutting edge.

13. The instrument of claim 1 wherein the sharp cutting edge comprises a circumferential cutting edge.

14. The instrument of claim 13 wherein the sharp cuffing edge is circular in shape.

15. The instrument of claim 1 wherein the sharp cutting edge is part-circumferential.

16. The instrument of claim 15 wherein the sharp cutting edge is circular in shape.

17. The instrument of claim 15 wherein the sharp cutting edge is oblong in shape.

18. The instrument of claim 1 wherein the outer member includes a shield portion extending distally from the sharp cuffing edge.

19. The instrument of claim 1, wherein the edge of the helical knife is configured to slice into cartilage.

20. The instrument of claim 19, wherein the edge of the helical knife is configured to slice into meniscal cartilage.

21. The instrument of claim 1, wherein the edge of the helical knife is configured to slice into fibroid tissue.

22. The instrument of claim 21, wherein the edge of the helical knife is configured to slice into intrauterine fibroid.

23. The instrument of claim 1, wherein the helical knife has a laterally facing cutting edge at the flat surface at the distal end of the helical knife.

24. A cutting instrument, comprising:
an outer member having an opening at least partially bounded by a cuffing edge; and
an inner member received in the outer member for rotation relative to the outer member, the inner member including a shaft having a helical knife defining a sharp, slicing edge, the helical knife having a flat surface at a distal end of the helical knife, the slicing edge having a V-shaped cross section perpendicular to a longitudinal extent of the slicing edge, wherein the cutting edge and the slicing edge are configured to interact to cut tissue.

25. The instrument of claim 24, wherein the helical knife is located at a distal portion of the inner member.

26. The instrument of claim 24 wherein a clearance between the inner member and the outer member is in the range of about 0.0005 to 0.002 inches.

27. The instrument of claim 24 wherein the inner member defines an aspiration opening, the aspiration opening being located at a proximal portion of the helical knife.

28. The instrument of claim 27, wherein the inner member has a wall defining a hollow interior, and the aspiration opening is defined through the wall of the inner member to the hollow interior.

29. The instrument of claim 24 wherein the helical knife includes a helical channel.

30. The instrument of claim 29 wherein the helical channel has a proximal end, a distal end, and a pitch, the pitch of the helical channel increasing from the distal end to the proximal end.

31. The instrument of claim 29 wherein a proximal end of the helical channel terminates in an opening through a wall of the inner member.

32. The instrument of claim 24, further comprising a hub coupling the inner member to the outer member, 33. The instrument of claim 24 wherein the outer member defines a fluid ingress opening through a wall of the outer member in a distal region of the outer member.

34. The instrument of claim 24 wherein the cutting edge is located at a distal portion of the outer member, 35. The instrument of claim 24 wherein the outer member tapers to the cutting edge.

36. The instrument of claim 24 wherein the cutting edge comprises a circumferential cutting edge.

37. The instrument of claim 36 wherein the cutting edge is circular in shape.

38. The instrument of claim 24 wherein the cutting edge is part-circumferential.

39. The instrument of claim 38 wherein the culling edge is circular in shape.

40. The instrument of claim 38 wherein the cutting edge is oblong in shape.

41. The instrument of claim 24 wherein the outer member includes a shield portion extending distally from the cutting edge.

42. The instrument of claim 24, wherein the helical knife has a laterally facing cutting edge at the flat surface at the distal end of the helical knife.

43. A cutting instrument comprising:
an outer member having an opening at least partially bounded by a sharp cutting edge; and
a helical knife coupled to the outer member for rotation relative to the outer member, the helical knife having a flat surface at a distal end of the helical knife, the helical knife configured to slice into tough, fibrous tissue, to draw the sliced tough, fibrous tissue into the opening, and to shear the sliced tough, fibrous tissue that has been drawn into the opening between the helical knife and the sharp cutting edge, the helical knife being arranged relative to the cutting edge such that portions of the helical knife and the cutting edge align in a plane substantially perpendicular to a longitudinal axis of the instrument to create the shearing therebetween.

44. The instrument of claim 43, wherein the helical knife is configured to slice into cartilage.

45. The instrument of claim 44, wherein the helical knife is configured to slice into meniscal cartilage.

46. The instrument of claim 43, wherein the helical knife is configured to slice into fibroid tissue.

47. The instrument of claim 46, wherein the helical knife is configured to slice into intrauterine fibroid, 48. The instrument of claim 43, further comprising:
an inner member received within the outer member, the helical knife being located at a distal portion of the inner member, the inner member having a wall defining a hollow interior; and
an aspiration opening being defined through the wall of the inner member to the hollow interior and being located at a proximal end of the helical knife.

49. The instrument of claim 43, wherein the helical knife has a laterally facing cutting edge at the flat surface at the distal end of the helical knife.

50. A culling instrument, comprising:
an outer member having an opening at least partially bounded by a sharp cutting edge;
a helical knife coupled to the outer member for rotation relative to the outer member, the helical knife having an edge configured to slice into tissue, the edge of the helical knife extending through the opening such that, during use, the edge slices into tissue to draw the tissue proximally along the helical knife towards the sharp cutting edge; wherein the sharp cutting edge and the edge of the helical knife are configured to cut tissue therebetween by a shearing action; and
an inner member received within the outer member, the helical knife being located at a distal portion of the inner member, the inner member having a wall defining a hollow interior, wherein the inner member defines an aspiration opening through the wall of the inner member to the hollow interior, the aspiration opening being located at a proximal portion of the helical knife, 51. A cutting instrument, comprising:
an outer member having an opening at least partially bounded by a sharp cutting edge; and
a helical knife coupled to the outer member for rotation relative to the outer member, the helical knife having an edge configured to slice into tissue, the edge of the helical knife extending through the opening such that, during use, the edge slices into tissue to draw the tissue proximally along the helical knife towards the sharp cutting edge; wherein the edge of the helical knife comprises a helical channel having a proximal end, a distal end, and a pitch, the pitch of the helical channel changing from the distal end to the proximal end.

52. The instrument of claim 51, further comprising:
an inner member received within the outer member, the helical knife being located at a distal portion of the inner member, the inner member having a wall defining a hollow interior; and
an aspiration opening being defined though the wall of the inner member to the hollow interior and being located at a proximal end of the helical knife.

53. A cutting instrument, comprising:
an outer member having an opening at least partially bounded by a cutting edge; and
an inner member received in the outer member for rotation relative to the outer member, the inner member including a shaft having a helical knife defining a sharp, slicing edge, the helical knife having a flat surface at a distal end of the helical knife, the slicing edge having a V-shaped cross section perpendicular to a longitudinal extent of the slicing edge, wherein the slicing edge is configured to draw tissue proximally along the helical knife towards the culling edge.

54. The instrument of claim 53, wherein the inner member has a wall defining a hollow interior, and an aspiration opening defined though the wall of the inner member to the hollow interior.

55. The instrument of claim 53, wherein the helical knife has a laterally facing cutting edge at the flat surface at the distal end of the helical knife.

56. A cutting instrument comprising:
an outer member having an opening at least partially bounded by a sharp cutting edge; and
a helical knife coupled to the outer member for rotation relative to the outer member, the helical knife having a flat surface at a distal end of the helical knife, the helical knife configured to draw tissue into the opening, and to shear the tissue that has been drawn into the opening between the helical knife and the sharp cutting edge, the helical knife being arranged relative to the cutting edge such tat portions of the helical knife and the cutting edge align in a plane substantially perpendicular to a longitudinal axis of the instrument to create the shearing therebetween.

57. The instrument of claim 56, further comprising:
an inner member received within the outer member, the helical knife being located at a distal portion of the inner member, the inner member having a wall defining a hollow interior; and
an aspiration opening being defined through the wall of the inner member to the hollow interior and being located at a proximal end of the helical knife.

58. The instrument of claim 56, wherein the helical knife has a laterally facing cutting edge at the flat surface at the distal end of the helical knife.

* * * * *

UNITED STATES PATENT AND TRADEMARK OFFICE
CERTIFICATE OF CORRECTION

PATENT NO. : 7,485,125 B2
APPLICATION NO. : 10/015778
DATED : February 3, 2009
INVENTOR(S) : Douglas D. Sjostrom It is certified that error appears in the above-identified patent and that said Letters Patent is hereby corrected as shown below:

In column 4, line 64 (claim 2), replace "though" with -- through --.

In column 5, line 30 (claim 12), replace "clalm" with -- claim --.

In column 5, line 34 (claim 14), replace "cuffing" with -- cutting --.

In column 5, line 45 (claim 18), replace "cuffing" with -- cutting --.

In column 5, line 59 (claim 24), replace "cuffing" with -- cutting --.

In column 6, line 23 (claim 32), replace "member," with -- member. --.

In column 6, line 28 (claim 34), replace "member," with -- member. --.

In column 6, line 37 (claim 39), replace "culling" with -- cutting --.

In column 7, line 2 (claim 47), replace "fibroid," with -- fibroid. --.

In column 7, line 14 (claim 50), replace "culling" with -- cutting --.

In column 7, line 32 (claim 50), replace "knife," with -- knife. --.

In column 8, line 1 (claim 52), replace "though" with -- through --.

In column 8, line 15 (claim 53), replace "culling" with -- cutting --.

In column 8, line 18 (claim 54), replace "though" with -- through --.

UNITED STATES PATENT AND TRADEMARK OFFICE
CERTIFICATE OF CORRECTION

PATENT NO. : 7,485,125 B2
APPLICATION NO. : 10/015778
DATED : February 3, 2009
INVENTOR(S) : Douglas D. Sjostrom It is certified that error appears in the above-identified patent and that said Letters Patent is hereby corrected as shown below:

In column 8, line 33 (claim 56), replace "tat" with -- that --.

Signed and Sealed this

Nineteenth Day of May, 2009

JOHN DOLL
*Acting Director of the United States Patent and Trademark Office*